United States Patent
Curtis et al.

(10) Patent No.: US 6,174,516 B1
(45) Date of Patent: Jan. 16, 2001

(54) METHOD TO ENHANCE PEROXIDE TOOTH WHITENING

(75) Inventors: John P. Curtis, Bloomsbury; Lisa Christina Beck, Burlington; Barry G. Reinhard, Annandale; Kedar N. Rustogi, Kendall Park, all of NJ (US)

(73) Assignee: Colgate-Palmolive Company, New York, NY (US)

( * ) Notice: Under 35 U.S.C. 154(b), the term of this patent shall be extended for 0 days.

(21) Appl. No.: 09/250,510

(22) Filed: Feb. 16, 1999

(51) Int. Cl.$^7$ .............................. A61K 7/16; A61K 7/20; A61K 33/40

(52) U.S. Cl. .............................. 424/53; 424/613; 424/616

(58) Field of Search .................................................. 424/53

(56) References Cited

U.S. PATENT DOCUMENTS

| | | | | |
|---|---|---|---|---|
| 4,657,758 | * | 4/1987 | Goldemberg et al. | 424/47 |
| 4,666,708 | * | 5/1987 | Goldemberg et al. | 424/49 |
| 4,976,955 | * | 12/1990 | Libin | 424/53 |
| 5,043,183 | * | 8/1991 | Gershon et al. | 424/52 |
| 5,256,402 | * | 10/1993 | Prencipe et al. | 424/53 |
| 5,338,538 | * | 8/1994 | Tricca et al. | 424/57 |
| 5,645,821 | * | 7/1997 | Libin | 424/49 |
| 5,698,182 | * | 12/1997 | Prencipe et al. | 424/53 |
| 5,814,304 | * | 9/1998 | Wong et al. | 424/53 |

* cited by examiner

Primary Examiner—Shep K. Rose
(74) Attorney, Agent, or Firm—Paul Shapiro

(57) ABSTRACT

A method is disclosed for effecting heightened whitening of teeth wherein there is first applied to the teeth an aqueous rinse composition having an alkaline pH and thereafter brushing the teeth with a peroxide dentifrice.

6 Claims, No Drawings

METHOD TO ENHANCE PEROXIDE TOOTH WHITENING

BACKGROUND OF THE INVENTION

1. Field of the Invention

This invention relates generally to method for whitening human teeth, and more particularly, to a method of whitening teeth by sequentially first applying to the teeth an alkaline rinse followed by brushing with a peroxide containing dentifrice.

2. The Prior Art

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate on the enamel layer of the tooth and form a film over the teeth. These staining and discoloring substances can then permeate the enamel layer. This problem occurs gradually over many years, but imparts a noticeable discoloration of the enamel of one's teeth.

Means known to the art to effect whitening of teeth include the application, as by brushing, to the teeth of peroxide containing dentifrice compositions of the type disclosed in U.S. Pat. No. 5,256,402 and U.S. Pat. No. 5,814,309.

The aqueous dentifrice compositions disclosed these patents contain a urea or hydrogen peroxide compound, an alkali pyrophosphate salt and an abrasive material. Although such peroxide dentifrice compositions of the prior art are effective in whitening teeth, the art continuously seeks means to effect even greater tooth whitening efficacy.

SUMMARY OF THE INVENTION

In accordance with the present invention it has now been found that the tooth whitening efficacy of peroxide containing dentifrice compositions can be substantially heightened by a method wherein there is first applied to the teeth an aqueous rinse composition having an alkaline pH of about 8.0 to about 11.0 and thereafter brushing the teeth to which the rinse has been previously applied with a peroxide containing dentifrice.

It is believed that the alkaline rinse application to the teeth prior to brushing with the peroxide dentifrice activates and promotes the rapid release of oxygen from the peroxide contained in the dentifrice, such rapid release accounting for the observed unexpected heightened whitening obtained by the brushing.

DETAILED DESCRIPTION OF THE INVENTION

The rinse formulations used in the practice of this invention comprise an alkaline solution having a pH of at least about 8.0 or above, and preferably about 8.5 to 10.5. The solvent for the rinse ingredients may be water or a solution of water and ethanol and such solvent generally comprises about 70% to about 95% of the rinse, and preferably about 65% to 95% water and about 0% to 35% ethanol.

Block polymers of polyoxyethylene and polyoxypropylene, such as available from BASF-Wyandotte Co., Wyandotte, Mich. are useful as surfactants in the preparation of the rinse and serve to solubilize flavor components as well as to provide foaming action while rinsing. In addition, other surfactants suitable for use in the preparation of the rinse composition include anionic surfactants such as sodium lauryl sulfate or sodium lauryl sulfonate. The surfactant is employed in the rinse composition at concentrations ranging from about 0.1% to about 10% by weight of the rinse, and most preferably from about 0.5% to abut 2% by weight.

Humectants such as glycerine and sorbitol in amounts up to about 25% by weight, and preferably about 15% to 20% by weight may also be used in the preparation of the rinse.

About 3 to about 10% by weight and preferably about 4 to about 8% by weight of an alkali metal such as sodium bicarbonate, sodium carbonate, sodium hydroxide and mixtures thereof are included in the rinse composition to adjust the pH to an alkaline range of about 8.0 to about 11.0 and preferably 9.0 to about 10.5.

Preservatives such as sodium benzoate, methylparaben, propylparaben and benzoic acid are included in the rinse compositions at concentrations of about 0.1 to about 1.0% by weight and preferably 0.4 to 0.6% by weight. Sodium benzoate is the preferred preservative.

Flavoring oils are incorporated in the rinse composition at a concentration of about 0.1 to 1.0% by weight, examples of which are oils of spearmint, peppermint, wintergreen, menthol, cineole, limonene, menthone and menthyl acetate.

A sweetening material is preferably also employed as a complement to the flavoring material. Suitable sweetening agents include sodium saccharine, sodium cyclamate, xylitol and aspartame in concentrations of about 0.01 to 1.0% by weight. Sodium saccharin is preferred.

The dental rinse is prepared by mixing the ingredients together to form a homogeneous solution of the constituent ingredients. The rinse is used by first applying a small amount in the mouth, such as one cap full, and rising about the tooth surfaces. As will hereinafter be demonstrated, a striking increase in whitening is observed over a relatively brief usage period when the rinse of this invention is first employed in sequential steps with a peroxide dentifrice.

The ingredients of the peroxide dentifrice composition used in the practice of the present invention are dissolved or suspended in a vehicle comprised of water and a humectant such as sorbitol polyethylene glycol or glycerin. Water constitutes about 10 to about 40% by weight of the peroxide dentifrice of the present invention and preferably about 20 to about 30% by weight.

Illustrative of polyethylene glycols useful in the practice of the present invention include polyethylene glycols known by the trademark Carbowax which are nonionic polymers of ethylene oxide having the general formula: $HOCH_2(CH_2OCH_2)_nCH_2OH$ wherein n represents the average number of oxyethylene groups. The Carbowax polyethylene glycols are designated by a number such as 400, 600, 800, 1000, 2000 which represents the average molecular weight. The molecular weight range of the polyethylene glycols used herein is about 200 to about 2000 and preferably about 600 hereinafter referred to as PEG 600.

The polyethylene glycol component included in the composition of the present invention constitutes about 10 to about 35% by weight of the dentifrice composition and preferably about 15 to about 25% by weight.

Glycerin is included in the dentifrice composition of the present invention in the range from 10 to about 20% by weight and preferably 12 to abut 15% by weight.

The peroxide compound used to prepare of the dentifrice composition used in the practice of the present invention is included in an amount sufficient to allow release of sufficient oxygen during brushing of teeth to effect whitening thereof. Typically, the peroxide compound is employed in the dentifrice composition in amounts so that at least about 1.0% of the composition comprises a peroxide. Preferably, the peroxide compound comprises from about 5 to about 15% by weight of the composition. Examples of suitable peroxide compounds used to prepare the dentifrice compositions used in the practice of the present invention include calcium peroxide, hydrogen peroxide and peroxides including urea peroxide, glyceryl peroxide, benzoyl peroxide and the like. A preferred peroxide compound is urea peroxide.

Abrasives suitable for use in the preparation of the dentifrice composition include silica, calcium pyrophosphate, dicalcium diphosphate and calcined alumina. The abrasive is incorporated in the dentifrice composition at a concentration of about 0 to 30% by weight and preferably about 5 to 10% by weight, Calcined alumina is a preferred abrasive.

Thickening agents are included in the peroxide compositions of the present invention in amounts from about 10% to about 25% by weight of the composition and preferably about 12 to about 20% by weight. Examples of suitable thickening agents include polyoxyethylene polyoxypropylene block copolymers having the formula $HO(C_2H_4O)_b(C_3H_6O)_a(C_2H_4O)_bH$ wherein a is an integer such that the hydrophobic base represented by $(C_3H_6O)$ has a molecular weight of about 2750 to 4000, b is an integer such that the hydrophilic portion represented by $(C_2H_4O)$ constitutes about 70–80% by weight of the copolymer. Block copolymers of this composition are available commercially under the trademark Pluronic F type. Pluronic F127, which has a molecular weight of range of about 9000 to about 14000 and contains 70% of the hydrophilic polyoxyethylene moiety is preferred for use as a gelling agent in the practice of the present invention.

Metal ion chelating agents when included in the peroxide dentifrice compositions used in the practice of the present invention contribute to the chemical stability of the peroxide composition when an abrasive such as calcined alumina or calcium pyrophosphate is also present in the dentifrice. Examples of suitable metal ion chelating agents include alkali metal stannates such as sodium and potassium stannate, ethylenediaminetetracetic acid (EDTA) and its salts. The metal ion chelating agents are incorporated in the dentifrice compositions of the present invention at a concentration of about 0.01 to about 1% by weight.

In preparing the peroxide compositions of the present invention, the pH of the composition is adjusted to a range between about 3.0 and about 8 and preferably about between about 5 and about 7 with an acid such as phosphoric acid.

Pyrophosphate salts having anti-tartar efficacy such as dialkali or tetra-alkali metal pyrophosphate salts such as $Na_4P_2O_7$, $K_4P_2O_7$, $Na_2K_2P_2O_7$, $Na_2H_2P_2O_7$, and $K_2H_2P_2O_7$, may be included in the dentifrice composition of the present invention at a concentration of about 0.5 to about 8.0% by weight and preferably about 1.5 to 5% by weight.

Fluoride salts having anti-caries efficacy may also be incorporated in the dentifrice composition of the present invention and are characterized by their ability to release fluoride ions in water, for example, sodium fluoride, potassium fluoride, sodium fluorosilicate, and sodium monofluorophosphate (NaMFP). It is preferable to employ a fluoride salt to release about 10 to about 1500 ppm of fluoride ion.

Flavor ingredients are incorporated in the peroxide dentifrice composition at a concentration of about 0.5–5.0% by weight. Suitable flavoring constituents are flavoring oils, e.g., oils of spearmint, peppermint, wintergreen, menthol, cineole, limonene, menthone and menthyl acetate.

A surfactant is also included in the dentifrice composition of the present invention and serves as a solubilizing, dispersing, emulsifying and wetting agent and is especially effective in solubilizing the flavor ingredient present. Surfactants which may be used in the practice of the present invention include cationic surfactants, anionic surfactants such as sodium laurylsulfate and sodium laurylsulfoacetate, ampholytic and amphoteric surfactants like cocoamidopropyl betaine.

A sweetening material is preferably also employed as a complement to the flavoring material. Suitable sweetening agents are water soluble and include sodium saccharin, sodium cyclamate, xylitol, aspartame and the like, in concentrations of about 0.01 to 1.0% by weight. Sodium saccharin is preferred.

To prepare the peroxide dentifrice compositions of the present invention, water soluble salts such as sodium saccharin and NaMFP are dissolved in an aqueous vehicle containing a humectant such as PEG 600 and glycerin. Followed by the addition of a polyoxyethylene-polyoxypropylene block copolymer gelling agent and the ingredients are mixed until a gel phase is formed. An abrasive compound such as calcium pyrophosphate is added to the gel and mixed to form a paste. The paste when formed is cooled to about 90–130° F., preferably about 100° F. A metal ion chelating agent, buffering agent and peroxide compound are then added to the paste and the ingredients mixed to obtain an homogenous mixture. The flavor and surfactant, are then added to the mixture to obtain a finished tooth whitening paste of the present invention.

The following Example further illustrates the present invention, but it is understood that the invention is not limited thereto. All amounts and proportions referred to herein and in the appended claims are by weight unless otherwise indicated.

EXAMPLE I

An alkaline rinse and a peroxide dentifrice used in the method of the present invention was prepared containing the ingredients listed in Tables I and II below.

TABLE I

| RINSE | |
|---|---|
| Ingredients | Wt. % |
| Ethyl Alcohol (95%) | 10.0 |
| Pluronic F108 | 1.0 |
| Pluronic F127 | 1.0 |
| Peppermint flavor | 0.150 |
| Purified water | 68.32980 |
| Glycerin | 15.0 |
| Sodium Bicarbonate | 4.0 |
| Sodium benzoate | 0.50 |
| Sodium saccharin | 0.020 |
| FD&C Green No. 3 color | 0.0002 |
| Total | 100.0 |

The rinse was prepared by dissolving in the ethanol/water mixture at room temperature the balance of the ingredients listed in Table I. The pH of the rinse was 8.5.

TABLE II

WHITENING DENTIFRICE

| Ingredients | Wt. % |
| --- | --- |
| Glycerin | 12.0 |
| PFG 600 | 15.0 |
| PEG 2000 | 6.0 |
| Purified water | 21.070 |
| Sodium saccharin | 0.50 |
| NaMFP | 0.760 |
| Pluronic F127 | 18.0 |
| Sodium Acid Pyrophosphate | 2.0 |
| EDTA - disodium dihydrate (99%) | 0.020 |
| Sodium lauryl sulfate | 0.80 |
| Flavor | 100.01.350 |
| Urea Peroxide | 10.0 |
| Phosphoric acid (85%) | 0.50 |
| Calcined alumina | 12.0 |
| Total | 100.00 |

The dentifrice composition was prepared by dispersing PEG 2000 in a mixture of PEG 600 and glycerin. Water was added to the mixture and the ingredients mixed for about 5 minutes. Sodium saccharin and sodium monofluorophosphate (NaMFP) were added and the resultant mixture stirred for 10 minutes, followed by the addition of Pluronic F127 and stirring for 1 hour. The mixture was then deaerated for 5 minutes and sodium acid pyrophosphate and calcined alumina were added and the resulting paste mixed for 15 minutes at high speed under vacuum. Urea peroxide was added to the paste which was further mixed for 10 minutes under vacuum at high speed. Flavor oil was then added to the paste and mixed under vacuum for 5 minutes. Sodium lauryl sulfate was then added under vacuum for 5 minutes at low speed. Phosphoric acid was added to adjust the pH of the composition to 4.0–5.0.

Twenty subjects determined by a dental examiner to demonstrate the presence of dental stain were provided with a package containing the rinse and peroxide dentifrice compositions of Tables I and II and a soft bristled adult toothbrush. Subjects were instructed to rinse with 5 ml of the rinse for 30 seconds immediately followed by brushing with the dentifrice for one minute, twice daily (morning and evening) for four weeks, without water rinsing between the rinse regimen and the dentifrice regimen.

The level of stain on the subjects teeth before the application of the rinse/dentifrice regimen or baseline and after two, three and four week intervals was evaluated using the Vita Shade Guide Method of Tooth Color Assessment. This standardized shade guide which is used by the dental profession includes sixteen different shades. Previous assessments of shade change using the brushing regimen alone without the benefit of the alkaline prerinse produced a shade change of 3.0 to 4.0, over the same 4 week period. The results of the present assessment are recorded in Table III below.

TABLE III

| Weeks of Treatment | Change from Baseline | Std. Deviation |
| --- | --- | --- |
| 2 | 5.9500 | 2.5438 |
| 3 | 7.1000 | 2.5935 |
| 4 | 8.4500 | 2.0641 |

The results recorded in Table III demonstrate that using the alkaline rinse prior to brushing with a peroxide dentifrice heightens the whitening effect observed over brushing alone producing a shade change of about 6 to about 8.5.

What is claimed is:

1. A method for effecting heightened whitening of teeth which comprises the sequential steps of first applying to the teeth an aqueous rinse composition having an alkaline pH of about 8.0 to about 10.5 which application is thereafter immediately folowed by brushing the teeth to which the rinse has been previously applied with a peroxide dentifrice to effect whitening of the teeth without water rinsing the teeth between the rinse regime and the dentifrice regime.

2. The method of claim 1 wherein the teeth are brushed with the dentifrice immediately following the application of the rinse.

3. The method of claim 1 wherein the peroxide is urea peroxide.

4. The method of claim 1 wherein the peroxide compound is present in the dentifrice composition at a concentration of about 1.0 to about 10% by weight of the composition.

5. The method of claim 1 wherein an abrasive is present in the dentifrice composition at a concentration of about 1 to about 30% by weight of the composition.

6. The method of claim 5 wherein the abrasive compound calcined alumina.

* * * * *